(12) United States Patent
Xiao et al.

(10) Patent No.: US 8,771,489 B2
(45) Date of Patent: Jul. 8, 2014

(54) CARBON MONOXIDE SENSOR WITH REDUCED HYDROGEN CROSS SENSITIVITY

(75) Inventors: Lei Xiao, London (GB); Terence Nicholas Moran, Portsmouth (GB)

(73) Assignee: Honeywell International Inc., Morristown, NJ (US)

( * ) Notice: Subject to any disclaimer, the term of this patent is extended or adjusted under 35 U.S.C. 154(b) by 158 days.

(21) Appl. No.: 13/342,369

(22) Filed: Jan. 3, 2012

(65) Prior Publication Data

US 2013/0168244 A1 Jul. 4, 2013

(51) Int. Cl.
*G01N 27/404* (2006.01)
*G01N 27/413* (2006.01)

(52) U.S. Cl.
USPC .......... 204/430; 73/23.31; 73/23.32; 204/431

(58) Field of Classification Search
CPC ........................... G01N 27/404; G01N 27/413
USPC ......... 204/406, 410, 411, 421–432; 73/23.31, 73/23.32; 205/781, 783.5–785, 787
See application file for complete search history.

(56) References Cited

U.S. PATENT DOCUMENTS

| | | | | |
|---|---|---|---|---|
| 4,810,352 A | * | 3/1989 | Bone et al. | 204/432 |
| 6,488,836 B1 | * | 12/2002 | Nakata et al. | 205/784 |
| 2003/0209442 A1 | * | 11/2003 | Harper | 205/108 |
| 2009/0057150 A1 | * | 3/2009 | Millar et al. | 204/432 |
| 2010/0236924 A1 | * | 9/2010 | Chapples et al. | 204/412 |

* cited by examiner

*Primary Examiner* — Jennifer Dieterle
(74) *Attorney, Agent, or Firm* — Wood, Phillips, Katz, Clark & Mortimer

(57) ABSTRACT

A gas sensor in one form comprises a housing including a base and a top defining an interior space. The housing includes a gas entry hole and first and second electrical terminals. First and second electrodes in the housing interior space each comprise a membrane having a layer of platinum black catalyst on one side. The second electrode includes a lower amount of platinum black catalyst than the first electrode. A separator is placed between the first and second electrodes. Current collectors electrically connect the first and second electrodes to the respective first and second electrical terminals whereby sensor current represents concentration of gas while minimizing cross sensitivity.

19 Claims, 2 Drawing Sheets

CARBON MONOXIDE SENSOR WITH REDUCED HYDROGEN CROSS SENSITIVITY

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD

This application relates to carbon monoxide sensing, and, more particularly, sensing carbon monoxide with reduced hydrogen cross sensitivity.

BACKGROUND

Electrochemical toxic gas sensors, in one form, are designed to be maintenance free and stable for long periods. They have a direct response to volume concentration of gas rather than partial pressure. The simplest form of electrochemical toxic gas sensor comprises two electrodes, a sensing electrode and a counter electrode separated by a thin layer of electrolyte. This structure is enclosed in a plastic housing that has a small capillary to allow gas entry to the sensing electrode and includes pins which are electrically attached to both electrodes and allow easy external interface. These pins may be connected to a simple resistor circuit that allows a voltage drop resulting from any current flow to be measured. Gas diffusing into the sensor is either oxidized or reduced at the sensing electrode and, coupled with a corresponding counter reaction at the other electrode, a current is generated through the external circuit. Since the rate of gas entering into the sensor is controlled by the capillary diffusion barrier, the current generated is proportional to the concentration of gas present outside the sensor and gives a direct measure of the toxic gas present.

One known carbon monoxide sensor suffers from a high or variable level of hydrogen cross sensitivity which can be an issue. A large variation has been observed, depending on catalyst batches used. Such a known sensor consists of a sensing electrode made from normal platinum and a counter electrode made from high surface area platinum and higher and weight of platinum. Two different catalysts were used to ensure that there was enough stability of potential and the like to last throughout the life of the product. Because the catalysts were not exactly matched there can be subtle but important differences in their behavior within the sensor environment.

The present disclosure is directed to improvements in cross sensitivity in a gas sensor.

SUMMARY

As described herein, cross sensitivity in a gas sensor is minimized by catalyst pairing selection.

A gas sensor in one form comprises a housing including a base and a top defining an interior space. The housing includes a gas entry hole and first and second electrical terminals. First and second electrodes in the housing interior space each comprises a membrane having a layer of platinum black catalyst on one side. The second electrode includes a lower amount of platinum black catalyst than the first electrode. A separator is placed between the first and second electrodes. Current collectors electrically connect the first and second electrodes to the respective first and second electrical terminals whereby sensor current represents concentration of gas while minimizing cross sensitivity.

It is a feature that the second electrode includes a center hole.

It is another feature to provide a dust cover overlying the gas entry hole.

It is a further feature that the first and second electrode membranes are circular and the layers of platinum black catalyst are also circular and of a smaller diameter than the membranes. Each membrane may have a diameter of about 18 mm and each layer of platinum black catalyst may have a diameter of about 12 mm. The center hole may have a diameter of about 3 mm.

It is another feature that the first electrode includes about 23 mg of platinum black catalyst and the second electrode includes about 20 mg of platinum black catalyst.

There is further disclosed a carbon monoxide sensor with minimum hydrogen cross sensitivity comprising a base having a bottom wall and a cylindrical side wall to define an interior space. The base includes first and second electrical terminals at the bottom wall. An electrode stack in the housing interior space comprises concentric circular stack layers including a seal layer, a lower separator layer, a counter electrode, an upper separator layer and a sensing electrode. The counter electrode comprises a membrane having a layer of platinum black catalyst. The sensing electrode comprises a membrane having platinum black catalyst. The counter electrode has a lower amount of platinum black catalyst than the sensing electrode. Current collectors electrically connect the counter and sensing electrodes to the respective first and second electrical terminals whereby sensor current represents concentration of carbon monoxide. A top is connected to the cylindrical side wall to close the interior space including a gas entry hole.

Other features and advantages will be apparent from a review of the entire specification, including the appended claims and drawings.

DETAILED DESCRIPTION

Figure 1:
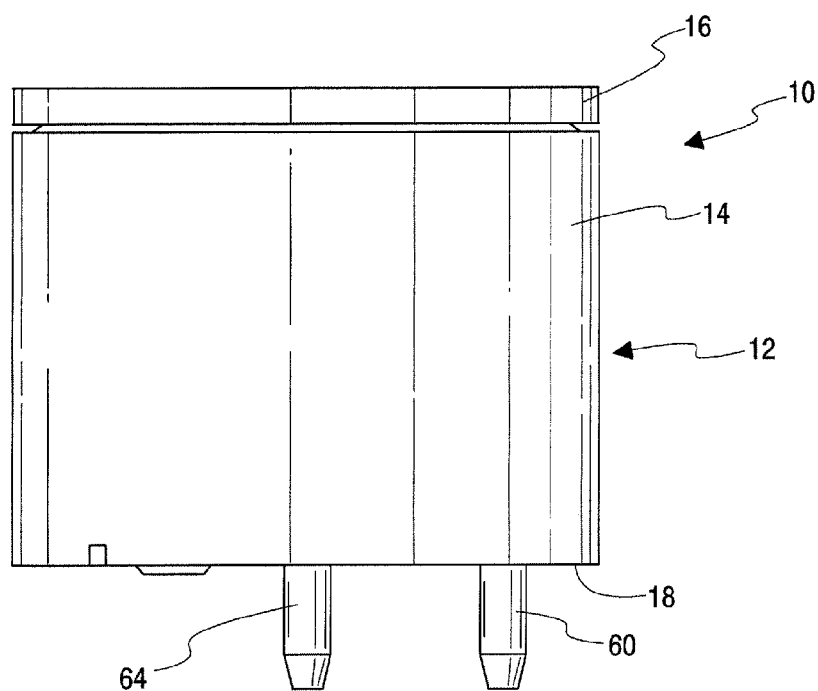
FIG. 1 is a side elevation view of a carbon monoxide sensor with reduced hydrogen cross sensitivity.
Figure 2:
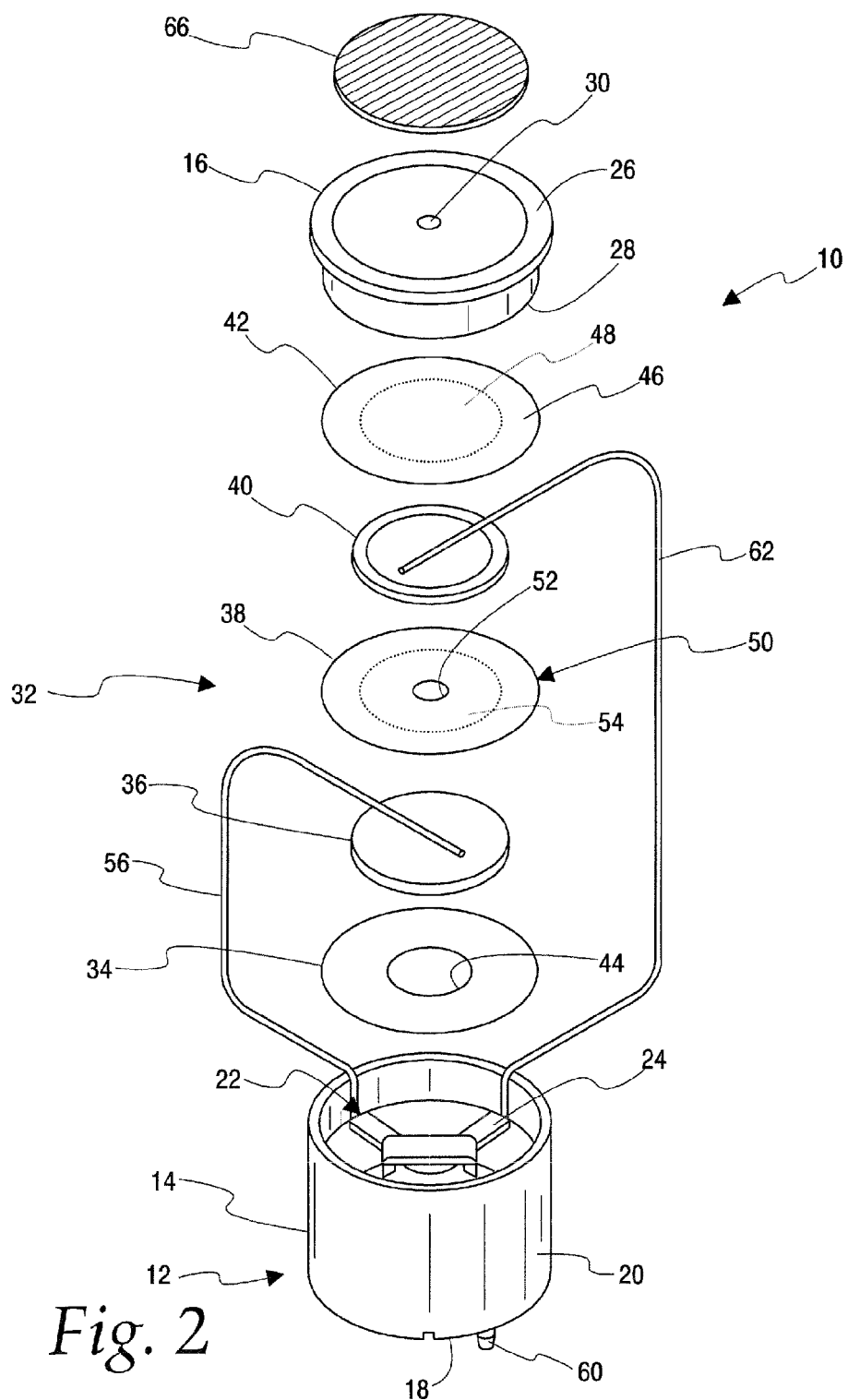
FIG. 2 is an exploded view of the carbon monoxide sensor of FIG. 1

Referring to FIGS. 1 and 2, a carbon monoxide sensor 10 is used for sensing carbon monoxide and is adapted to minimize hydrogen cross sensitivity. As will be apparent, the principles disclosed herein could be used to minimize cross sensitivity in other types of gas sensors.

The sensor 10 comprises a housing 12 including a base 14 and a top 16. The base 14 comprises a bottom wall 18 and a cylindrical side wall 20 to define an interior space 22. The base 14 includes support elements 24 spaced above the bottom wall 18. The top 16 includes a circular top wall 26 and a downwardly depending neck 28 of narrower diameter to be telescopically received in the base 14. The top includes a gas entry opening 30.

The housing 12 encloses an electrode stack 32. The electrode stack 32 comprises concentric circular stack layers including a base seal layer 34, a lower separator 36, a counter electrode 38, an upper separator 40 and a sensor electrode 42. In the illustrated embodiment, the lower separator 36 is thicker than the upper separator 40.

The base seal layer 34 includes a central opening 44 and rests on the support structure 24 generally proximate the bottom wall 18. The lower separator layer 36 is atop the base seal layer 34. The counter electrode 38 is atop the lower separator layer 36. The upper separator layer 40 is atop the counter electrode. The sensor electrode 42 is atop the upper separator layer 40.

The sensor electrode 42 comprises a circular membrane 46. The membrane 46 comprises a porous hydrophobic membrane. A layer of platinum black catalyst 48 is on a lower side of the membrane 46 in a circular area of a smaller diameter than the diameter of the membrane 46.

The counter electrode 38 includes a membrane 50, similar to the upper electrode membrane 46, and further comprising a center hole 52. A layer of platinum black catalyst 54 is on a lower side of the membrane 50 in a circular area of smaller diameter than the diameter of the membrane 50. In fact, the counter electrode 38 is the same as the sensing electrode 42, except that the counter electrode 38 includes the center hole 52. As a result, the counter electrode 38 includes a lower amount of platinum black catalyst than the sensing electrode 42.

The sensor 10 as described herein uses catalyst of the same or similar surface area for both electrodes 38 and 42, with weight of the catalyst of the counter electrode 38 being lower.

A first current collector 56 electrically connects the counter electrode 38 to a first electrical terminal in the form of a pin 60. A second current collector 62 electrically connects the sensor electrode 42 to a second electrical terminal in the form of a second pin 64. The current collectors 56 and 62 are flat and are placed across the center and do not extend beyond the catalyst area. Particularly, the first current collector 56 is sandwiched between the lower separator 36 and the catalyst layer 54 of the counter electrode 38. The second current collector 62 is sandwiched between the upper separator 40 and the catalyst layer 48 of the sensor electrode 42.

In an exemplary embodiment of the invention, the membranes 46 and 50 are about 18 mm diameter and the catalyst layers 48 and 54 are about 12 mm diameter. The counter electrode center opening 52 is about 3 mm. The sensor electrode 42 catalyst layer 48 includes about 23 mg of platinum black. The counter electrode catalyst layer 54 includes about 20 mg of platinum black.

In the illustrated embodiment, the electrical terminals 60 and 64 comprise pins which extend from the bottom wall 18. Alternatively, electrical terminals could be surface pads or the like for connecting to external circuitry.

As it is apparent, the specific dimensions of the components of the electrode stack 32 could vary in both size as well as shape.

The illustrated sensor 10 comprises a two electrode sensor. As will be apparent, the disclosed techniques could be applied to three electrode sensors which further include a reference electrode.

The electrode stack 32 is positioned in the interior space 22 on the support surface 24. When the top 16 is telescopically received in the base side wall 20, the electrode stack 32 is sandwiched therebetween. The top 16 is secured to the base side wall 20 such as by ultrasonic welding. Alternatively, laser welding, thermal welding, compression seals with bolted components and other closure methods could be used. A dust cover 66 is secured to the top wall 26 overlying the gas entry opening 30.

Gas diffusing into the sensor 10 is either oxidized or reduced at the sensing electrode catalyst layer 48 and, coupled with a corresponding counter reaction at the counter electrode catalyst layer 54, a current is generated through an external circuit. Since the rate of gas entering into the sensor 10 is controlled by the capillary in the form of the gas entry opening 30, the current generated is proportional to the concentration of gas present outside the sensor 10 and gives a direct measure of the toxic gas present. The catalyst pairing selection as described herein results in a gas sensor with reduced cross sensitivity, particularly reduced hydrogen cross sensitivity.

The sensor 10 may be connected to a load resistor across which is developed a voltage proportional to the output current and hence proportional to the gas concentration. The resistor typically has a value between 10 and 100 ohms and its value is chosen to provide a suitable magnitude of voltage output without being so large as to slow down the sensor response. Other methods of measuring the sensor current can also be used.

It will be appreciated by those skilled in the art that there are many possible modifications to be made to the specific forms of the features and components of the disclosed embodiments while keeping within the spirit of the concepts disclosed herein. Accordingly, no limitations to the specific forms of the embodiments disclosed herein should be read into the claims unless expressly recited in the claims. Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A carbon monoxide sensor with minimal hydrogen cross sensitivity comprising:
a base comprising a bottom wall and a cylindrical side wall to define an interior space, the base including first and second electrical terminals;
an electrode stack in the housing interior space comprising concentric circular stack layers including a counter electrode, a sensing electrode and a thin separator layer between the counter electrode and the sensing electrode, the counter electrode comprising a membrane having a layer of platinum black catalyst, and the sensing electrode comprising a membrane having a layer of platinum black catalyst, wherein the counter electrode includes a lower amount of platinum black catalyst than the sensing electrode;
current collectors electrically connecting the counter and sensing electrodes to the respective first and second electrical terminals whereby sensor current represents concentration of carbon monoxide; and
a top connected to the cylindrical sidewall to close the interior space and including a gas entry hole.

2. The carbon monoxide sensor of claim 1 wherein the electrode stack further comprises a seal layer proximate the bottom wall, and a lower separator layer between the seal layer and the counter electrode.

3. The carbon monoxide sensor of claim 2 wherein one of the current collectors is sandwiched between the sensing electrode and the thin separator layer and another current collector is sandwiched between the counter electrode and the lower separator layer.

4. The carbon monoxide sensor of claim 3 wherein the one current collector extends across a center of the counter electrode and the another current collector extends across a center of the sensing electrode.

5. The carbon monoxide sensor of claim 2 wherein the lower separator layer is thicker than the thin separator layer.

6. The carbon monoxide sensor of claim 1 wherein the base and the top are of plastic construction and the top is ultrasonically welded to the base.

7. The carbon monoxide sensor of claim 1 further comprising a dust cover on the top overlying the gas entry hole.

8. The carbon monoxide sensor of claim 1 wherein the electrode membranes are circular and the platinum black catalyst of each electrode is in a circular area of a smaller diameter area than a diameter of the membranes.

9. The carbon monoxide sensor of claim 8 wherein the circular area of the counter electrode is substantially the same as circular area of the sensing electrode.

10. The carbon monoxide sensor of claim 8 wherein each membrane has a diameter of about 18 mm and each circular area of platinum black catalyst has a diameter of about 12 mm.

11. The carbon monoxide sensor of claim 10 wherein the counter electrode includes a center hole having a diameter of about 3 mm.

12. The carbon monoxide sensor of claim 1 wherein the sensing electrode includes about 23 mg of platinum black catalyst and the counter electrode includes about 20 mg of platinum black catalyst.

13. A gas sensor comprising:
a housing including a base and a top defining an interior space, the housing including a gas entry hole and first and second electrical terminals extending from the housing;
first and second electrodes in the housing interior space each comprising a membrane having a layer of platinum black catalyst on one side, the second electrode includes a lower amount of platinum black catalyst than the first electrode;
a separator placed between the first and second electrodes; and
current collectors electrically connecting the first and second electrodes to the respective first and second electrical terminals whereby sensor current represents concentration of gas while minimizing cross sensitivity.

14. The gas sensor of claim 13 wherein the second electrode includes a center hole.

15. The gas sensor of claim 13 further comprising a dust cover overlying the gas entry hole.

16. The gas sensor of claim 13 wherein the first and second electrode membranes are circular and the layers of platinum black catalyst are also circular and of a smaller diameter area than the membranes.

17. The gas sensor of claim 16 wherein each membrane has a diameter of about 18 mm and each layer of platinum black catalyst has a diameter of about 12 mm.

18. The gas sensor of claim 17 wherein the counter electrode comprises a center hole having a diameter of about 3 mm.

19. The gas sensor of claim 13 wherein the first electrode includes about 23 mg of platinum black catalyst and the second electrode includes about 20 mg of platinum black catalyst.

* * * * *